United States Patent
Piantoni et al.

(10) Patent No.: US 10,478,348 B2
(45) Date of Patent: Nov. 19, 2019

(54) UNIT FOR FEEDING A COMPONENT OF A HYGIENE ABSORBENT ARTICLE PROVIDED WITH A LINEAR ELECTRIC MOTOR

(71) Applicant: GDM S.P.A., Bologna (IT)

(72) Inventors: Matteo Piantoni, Albino (IT); Valerio Soli, Bologna (IT); Marco Rosani, Vailate (IT); Federico Tordini, Pedrengo (IT); Massimo Pallavera, Soresina (IT)

(73) Assignee: GDM S.p.A., Bologna (IT)

( * ) Notice: Subject to any disclaimer, the term of this patent is extended or adjusted under 35 U.S.C. 154(b) by 0 days.

(21) Appl. No.: 16/084,274

(22) PCT Filed: Mar. 17, 2017

(86) PCT No.: PCT/IB2017/051574
§ 371 (c)(1),
(2) Date: Sep. 12, 2018

(87) PCT Pub. No.: WO2017/158572
PCT Pub. Date: Sep. 21, 2017

(65) Prior Publication Data
US 2019/0060134 A1    Feb. 28, 2019

(30) Foreign Application Priority Data

Mar. 18, 2016    (IT) ..................... 102016000028768

(51) Int. Cl.
*A61F 13/15*    (2006.01)
*B65G 47/84*    (2006.01)

(52) U.S. Cl.
CPC .. *A61F 13/15764* (2013.01); *A61F 13/15804* (2013.01); *B65G 47/848* (2013.01); *A61F 2013/15821* (2013.01)

(58) Field of Classification Search
CPC ..... B65G 47/848; B65G 47/244; A61F 13/15; A61F 13/15764; A61F 13/15804;
(Continued)

(56) References Cited

U.S. PATENT DOCUMENTS

| | | | | |
|---|---|---|---|---|
| 4,856,397 A * | 8/1989 | Rebekale | ................. | B26D 1/62 83/322 |
| 6,705,453 B2 * | 3/2004 | Blumenthal | ...... | A61F 13/15764 198/471.1 |
| 6,719,031 B2 * | 4/2004 | Sawai | ................. | A61F 13/0279 156/519 |
| 8,100,253 B2 * | 1/2012 | Walsh | ............... | A61F 13/15764 198/377.08 |

(Continued)

FOREIGN PATENT DOCUMENTS

| | | |
|---|---|---|
| EP | 1726414 A1 | 11/2006 |
| EP | 1961403 A2 | 8/2008 |

(Continued)

OTHER PUBLICATIONS

International Application No. PCT/IB2017/051574, International Search Report and Written Opinion, dated Jun. 27, 2017.

*Primary Examiner* — James R Bidwell
(74) *Attorney, Agent, or Firm* — Marshall, Gerstein & Borun LLP (57) ABSTRACT

A feeding unit for feeding a component of a hygiene absorbent article; the feeding unit has: at least one sucking-holding head, which is designed to receive and hold the component; a conveyor to cyclically move the holding head along an annular application path; an input station in which the holding head receives a corresponding component which is connected—without gaps—to a continuous web; a cutting station provided with a cutting device, which cuts the continuous web crosswise; and an output station in which the holding head releases the component; the conveyor has:

(Continued)

an annular guide; a slide which supports the holding head and is coupled to the guide so as to freely slide along the guide itself; and a linear electric motor, which has a stator, which is arranged in a fixed position along the guide and a mobile slider which is electro-magnetically coupled to the stator so as to receive, from the stator, a driving force and is rigidly connected to the slide.

17 Claims, 12 Drawing Sheets

(58) Field of Classification Search
CPC ............. Y10T 83/4833; Y10T 83/4838; Y10T 83/485; Y10T 83/207
USPC ........ 198/471.1, 478.1, 397.04, 397.05, 400, 198/377.08, 377.02, 459.8; 83/343, 344, 83/346
See application file for complete search history.

(56) References Cited

U.S. PATENT DOCUMENTS

| | | | | |
|---|---|---|---|---|
| 8,720,666 | B2 * | 5/2014 | Papsdorf | A61F 13/15764 198/377.02 |
| 8,820,513 | B2 * | 9/2014 | Papsdorf | A61F 13/15764 198/478.1 |
| 9,511,952 | B1 * | 12/2016 | Schneider | B65G 47/244 |
| 9,693,909 | B2 * | 7/2017 | Tombuelt-Meyer | A61F 13/15764 |
| 2004/0089516 | A1 * | 5/2004 | Christian | A61F 13/15723 198/459.8 |

FOREIGN PATENT DOCUMENTS

| | | | |
|---|---|---|---|
| EP | 2644174 A1 | 10/2013 | |
| WO | WO-2008/155618 A2 | 12/2008 | |
| WO | 2014/167369 * | 10/2014 | ............. B65G 29/00 |
| WO | WO-2015/159204 A1 | 10/2015 | |

* cited by examiner

UNIT FOR FEEDING A COMPONENT OF A HYGIENE ABSORBENT ARTICLE PROVIDED WITH A LINEAR ELECTRIC MOTOR

CROSS-REFERENCE TO RELATED APPLICATIONS

This is U.S. national phase of International Application No. PCT/IB2017/051574, filed Mar. 17, 2017, which claims the benefit of Italian Patent Application No. 102016000028768, filed Mar. 18, 2016.

TECHNICAL FIELD

The present invention relates to a unit for feeding a component of a hygiene absorbent article.

PRIOR ART

As known, the hygiene absorbent articles comprise an impermeable layer (e.g. polyethylene), a non-woven fabric layer permeable to liquids, and an absorbent padding enclosed therebetween. Said components are the basic elements of an absorbent article. In addition to the basic components mentioned above, the absorbent articles further comprise accessory components (such as elastic bands, faecal barriers and lateral wings) which make the structure, as well as the manufacturing, more or less complex.

A known type of maker machine for manufacturing hygiene absorbent articles comprises a feeding line of a continuous web of impermeable material along which a plurality of operating units are arranged which feed the basic and accessory components, intended to define the absorbent article, to the continuous web.

Each operating unit comprises a feeding unit provided with a main drum (hinged so as to rotate with a continuous motion around a central rotation axis) which supports a plurality of sucking-holding heads, each of which is designed to receive and hold a corresponding component which is separated, by a crosswise cut, from a continuous web. In an input station, each sucking-holding head receives a corresponding component which is still an integral part of the continuous web (i.e. forms the final end of the continuous web) and is subsequently separated from the continuous web by means of a crosswise cut performed by a cutting device arranged downstream from the input station. According to a possible embodiment, downstream from the cutting device each head can be rotated by 90° so as to vary the orientation of the component. Finally, in an output station each sucking-holding head releases the corresponding component.

In the known feeding units (for example as described in the patent applications EP1726414A1 and EP1961403A2), the cutting device comprises at least one blade and at least one counter-blade (i.e. an anvil) cooperating one with the other to perform in a "guillotine-like" manner the crosswise cut of the continuous web; in other words, the blade is pushed against the counter-blade with the interposition of the continuous web so as to obtain the crosswise cut of the continuous web itself. In the known feeding unit, a cutting drum is provided which supports the blade and is arranged parallel and beside the main drum, and a counter-drum which supports a plurality of counter-blades, is arranged parallel to and inside the main drum, and is arranged facing the cutting drum so that a blade of the cutting drum can cyclically cooperate with a counter-blade of the counter-drum so as to perform the crosswise cut of the continuous web. To avoid that the counter-blades may constitute an obstacle for the rotation of the sucking-holding head (i.e. that a sucking-holding head by rotating of 90°, after the separation of the corresponding component from the continuous web, can "slam" against a counter-blade), in the known feeding units (for example as described in patent applications EP1726414A1 and EP1961403A2) the counter-drum is offset (eccentric) relative the main drum so that the counter-blades are close to the sucking-holding heads at the cutting area and are spaced apart from the corresponding sucking-holding heads at the rotation area of the sucking-holding heads themselves.

However, with this configuration the known feeding unit have a relatively complex and expensive structure because it is necessary to integrate, in the same relatively narrow space, two rotating units (the main drum and the counter-drum) separate and independent one from the other. In addition, with this configuration the known feeding unit complicate a format change operation, i.e. an operation which modifies the maker machine so as to vary the type of hygiene absorbent articles which are manufactured, as it is necessary to modify the shape and/or the laws of rotational motion of two units (the main drum and the counter-drum) separate and independent one from the other but substantially integrated in the same space.

DESCRIPTION OF THE INVENTION

Purpose of the present invention is to provide a unit for feeding a component of a hygiene absorbent article that is free from the drawbacks described above and, at the same time, is simple and inexpensive to manufacture.

According to the present invention a unit for feeding a component of a hygiene absorbent article is provided, as claimed in the appended claims.

BRIEF DESCRIPTION OF DRAWINGS

The present invention will now be described with reference to the accompanying drawings, which illustrate some examples of non-limiting embodiments, wherein.

PREFERRED EMBODIMENTS OF THE INVENTION

In FIGS. 1-4, number 1 denotes as a whole a unit 1 for feeding a component 2 of a hygiene absorbent article. The feeding unit 1 is part of a maker machine for manufacturing hygiene absorbent articles.

Each component 2 is obtained from a continuous web 3 (unwound from a spool) by means of a crosswise cut of the continuous web 3; namely the continuous web 3 is cyclically cut crosswise to separate in one after the other the individual components 2 from the continuous web 3.

The feeding unit 1 comprises a plurality of sucking-holding heads 4 each designed to receive and hold a corresponding component 2 and a conveyor 5 that supports the sucking-holding heads 4 and moves cyclically each sucking-holding head 4 along an annular application path P (illustrated in FIG. 4) which passes through an input station S1 in which the sucking-holding head 4 receives a corresponding component 2 still connected to the continuous web 3 and an output station S2 in which the sucking-holding head 4 releases the component 2 to a subsequent device 6.

In FIGS. 1-4, the device 6 is schematically illustrated as a belt conveyor, but it is evident that the device 6 which receives in succession the components 2 in the output station S2 can be any type of device of a maker machine for manufacturing hygiene absorbent articles.

Between the input station S1 and output station S2 (i.e. downstream from the input station S1 and upstream from the output station S2) a cutting station S3 is arranged in which the continuous web 3 is cyclically cut crosswise so as to separate the components 2, held by the sucking-holding heads 4, from continuous web 3. Hence, when in the input station S1 a component 2 is initially engaged by a corresponding sucking-holding head 4, the component 2 itself is still part of the continuous web 3 (i.e. is connected—without gaps—to the continuous web 3) and is separated from the continuous web 3 itself by means of a crosswise cut in the cutting station S3 arranged, i.e. downstream from the input station S1.

According to a preferred (but not binding) embodiment, between the cutting station S3 and the output station S2 (i.e. downstream from the cutting station S3 and upstream from the output station S2) a rotation station S4 is arranged, in which each sucking-holding head 4 rotates by 90° (or, alternatively, of any other angle other than 90°) relative to the conveyor 5 and around the rotation axis 7 (illustrated in FIGS. 5, 6 and 7) radially arranged (i.e. perpendicular) to the application path P. In other words, each sucking-holding head is mounted to rotate on itself around a rotation axis 7 radially arranged (i.e. perpendicular) to the application path P. In use, in the rotation station S4 each sucking-holding head 4 carrying a component 2 performs a 90° rotation around the corresponding rotation axis 7 so as to change the orientation of the component 2 carried by the sucking-holding head 4 itself; between the output station S2 and the input station S1 each sucking-holding head 4 devoid of the component 2 performs a counter-rotation (i.e. a rotation in the opposite direction) by 90° around the corresponding rotation axis 7 to return to the departure position prior to receiving a new component 2.

The conveyor 5 comprises an annular guide 8 (i.e. closed in a ring-like manner) which is arranged in a fixed position along the application path P; in particular, the annular guide 8 is formed by a single fixed rail (i.e. devoid of movement) which is arranged along the application path P. In addition, the conveyor 5 comprises a plurality of slides 9, each of which supports a corresponding sucking-holding head 4 and is coupled to the guide 8 so as to freely slide along the guide 8 itself. Finally, the conveyor 5 comprises a linear electric motor 10 which moves the slides 9 carrying the sucking-holding heads 4 along the application path P; the linear electric motor 10 comprises an annular stator 11 (i.e. a fixed primary one) arranged in a fixed position along the guide 8 and a plurality of mobile sliders 12 (i.e. mobile secondary ones), each of which is electro-magnetically coupled to the stator 11 to receive from the stator 11 itself a driving force and is rigidly connected to a corresponding slide 9.

The stator 11 of the linear electric motor 10 comprises a ferromagnetic armature having a series of grooves housing the windings which are suited to be crossed by electric currents variable over time so as to generate corresponding stator magnetic fields (variable over time); each slider 12 of the linear electric motor 10 comprises a ferromagnetic armature in which at least one permanent magnet is arranged, which generates a rotor magnetic field (constant in time), which interacts with the stator magnetic field so as to generate, on the slider 12, a driving force of electromagnetic source. In each slide 9, the slider 12 is mounted so as to be in close proximity (indicatively 1-2 mm) with the stator 11 to minimize the air gap existing between the ferromagnetic armature of the slider 12 and the ferromagnetic armature of the stator 11.

A control device 10 is provided, which drives the linear electric motor by applying a variable voltage to the windings of the stator 11. Preferably, the control device uses a closed loop control system (i.e. feedback type) to control the position of each slider 12 (and therefore of each slide 9). Consequently, the control device must know in real time and with high precision the actual location of each slider 12 (and therefore of each slide 9) along the application path P; for this purpose, the control device can reconstruct the actual position of each slider 12 along the application path P by means of estimation algorithms based on the electrical signals at the terminals of the windings of the stator 11 or the control device can receive the detection of a specific position sensor which is arranged along the application path P. For example, the position sensor comprises a measuring ring made of magnetostrictive material which is arranged along the application path P and, for each slider 12, a corresponding permanent magnet that is arranged next to the measuring ring.

As previously mentioned, each sucking-holding head 4 is fitted on the corresponding slide 9 in a rotary manner, so as to rotate around a rotation axis 7; the conveyor 5 comprises a cam operating system so as to control the rotation of each sucking-holding head 4 around the rotation axis 7. According to what is illustrated in FIGS. 5, 6 and 7, the cam operating system comprises a cam 13 (illustrated in FIGS. 1, 2 and 3) arranged in a fixed position beside the guide 8 and along the application path P and, for each holding head 4, a corresponding cam follower roller 14 which is coupled to the cam 13 (i.e. slides on the cam 13 to follow the profile of the cam 13 itself) and is mechanically connected to the sucking-holding head 4.

Figure 5:
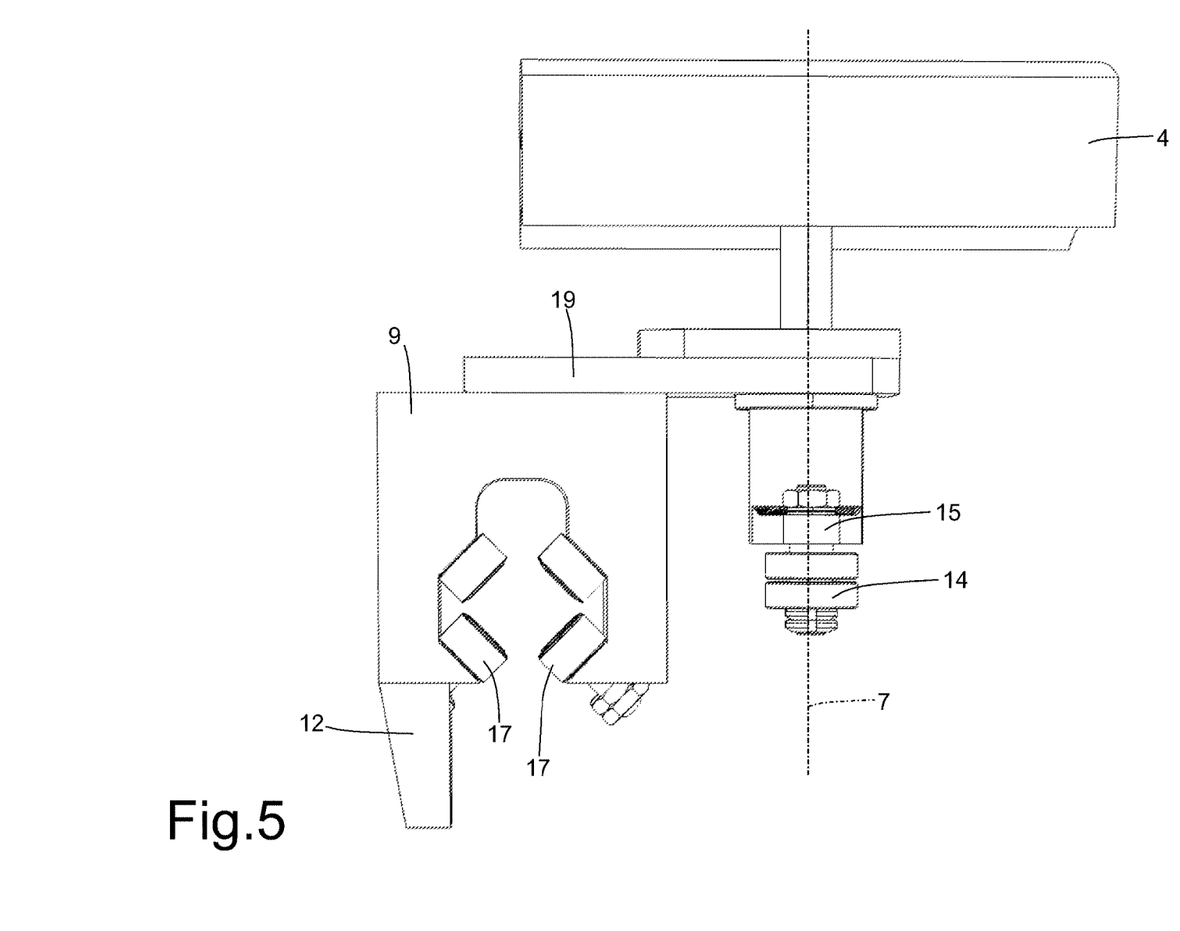
FIG. 5 is a side view of a mobile assembly of the feeding unit of FIG. 1.
Figure 6:
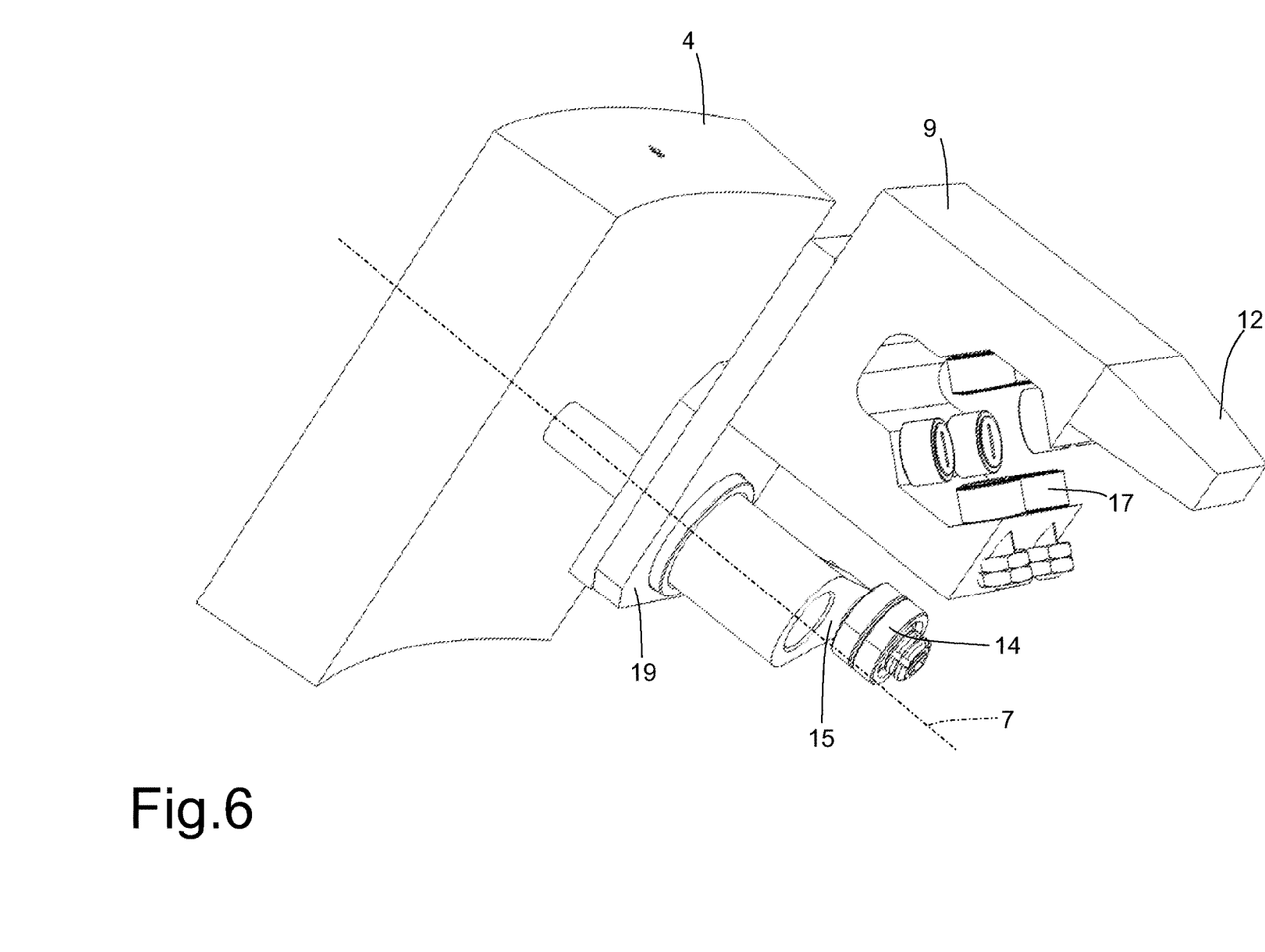
FIGS. 6 and 7 are two different perspective views of the mobile assembly of FIG. 5.
Figure 7:
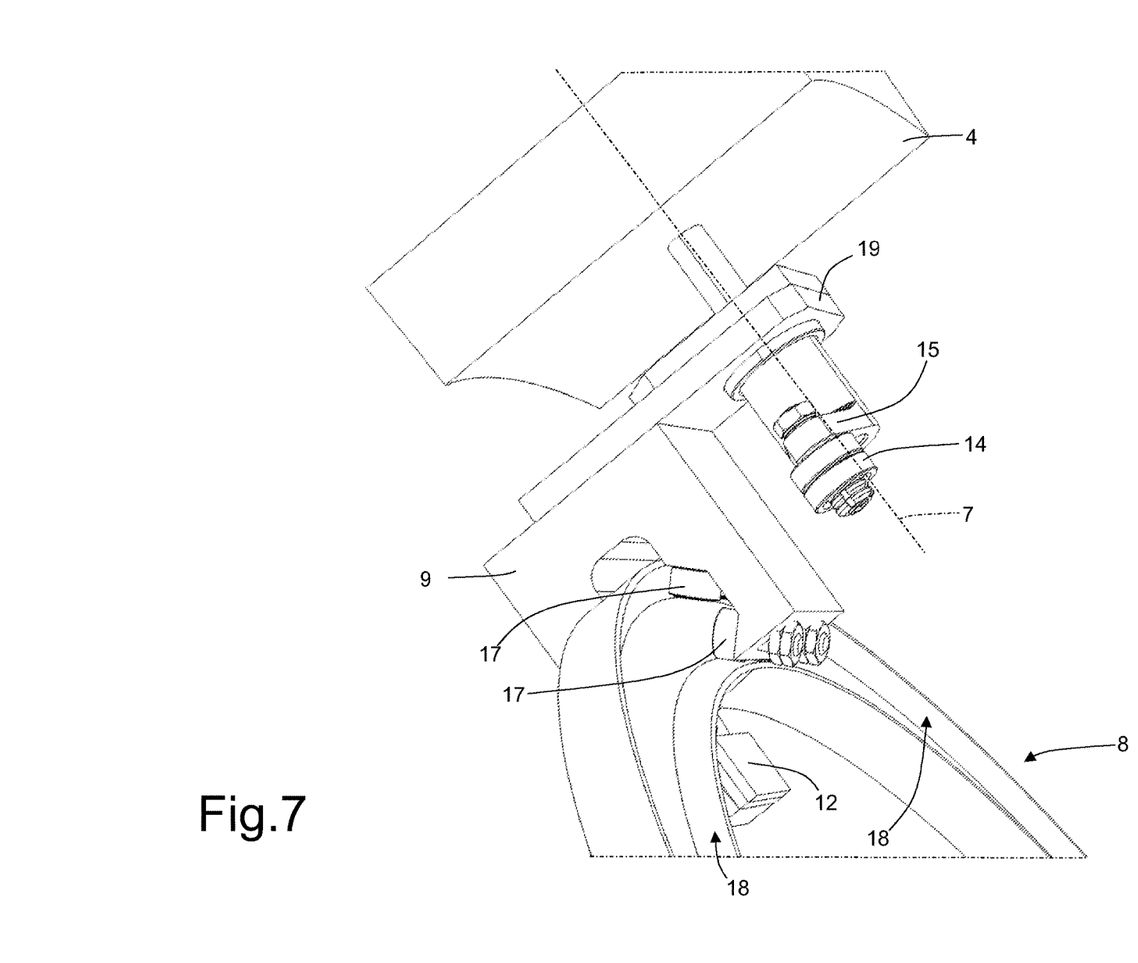

According to what is illustrated in FIGS. 5, 6 and 7, in each slide 9, the cam follower roller 14 is oriented parallel to the rotation axis 7; furthermore, an operating arm 15 is provided, having a first end on which the cam follower roller is fitted in a rotary manner and a second end which is angularly integral with the sucking-holding head 4. In this embodiment, one end of each operating arm 15 is directly bound to a shaft which supports the sucking-holding head 4 in such a way that the rotational movement of the operating arm 15 becomes equal to the rotary movement of the sucking-holding head 4.

Figure 1:
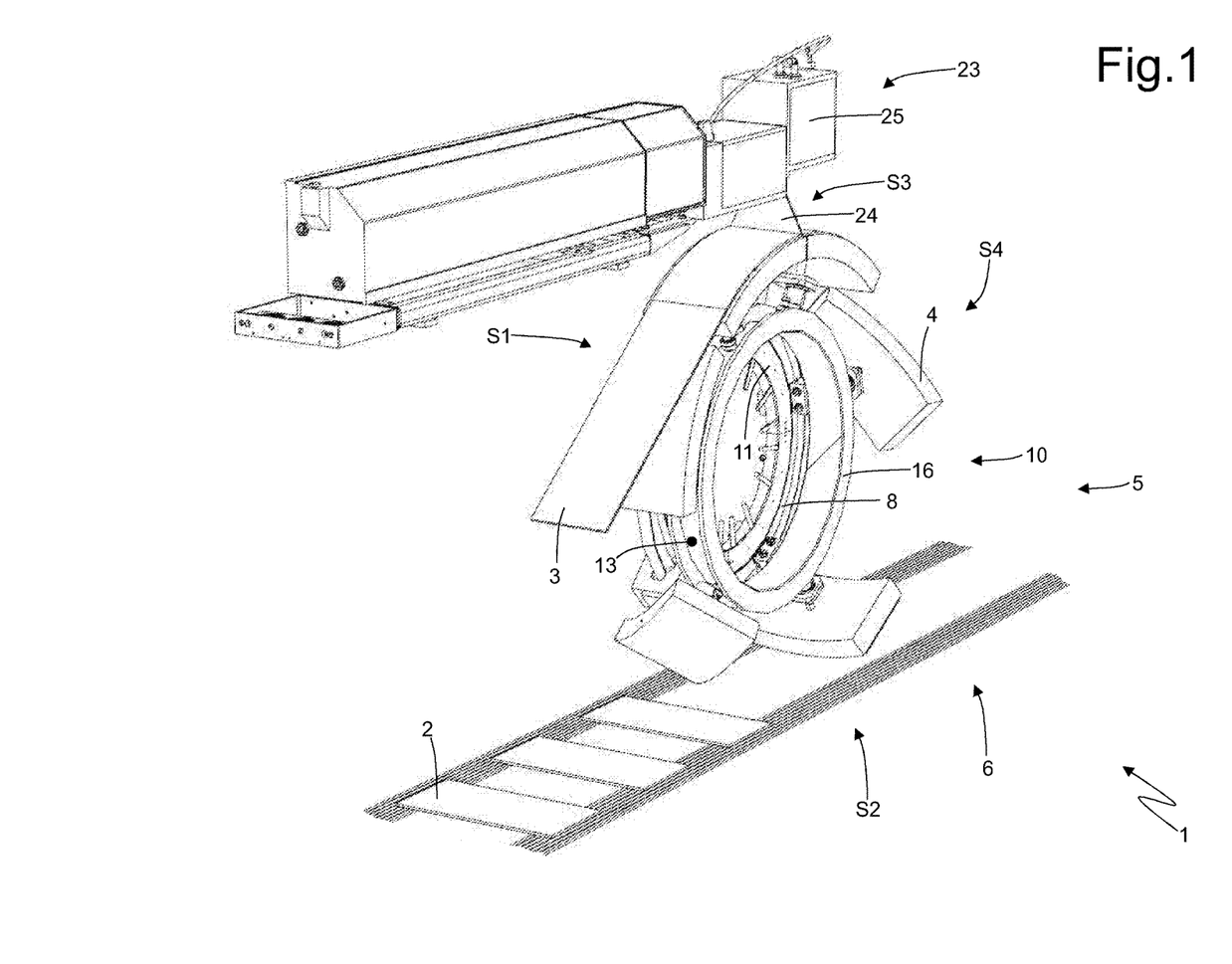
FIG. 1 is a perspective and schematic view of a feeding unit of a component of a hygiene absorbent article manufactured according to the present invention.
Figure 2:
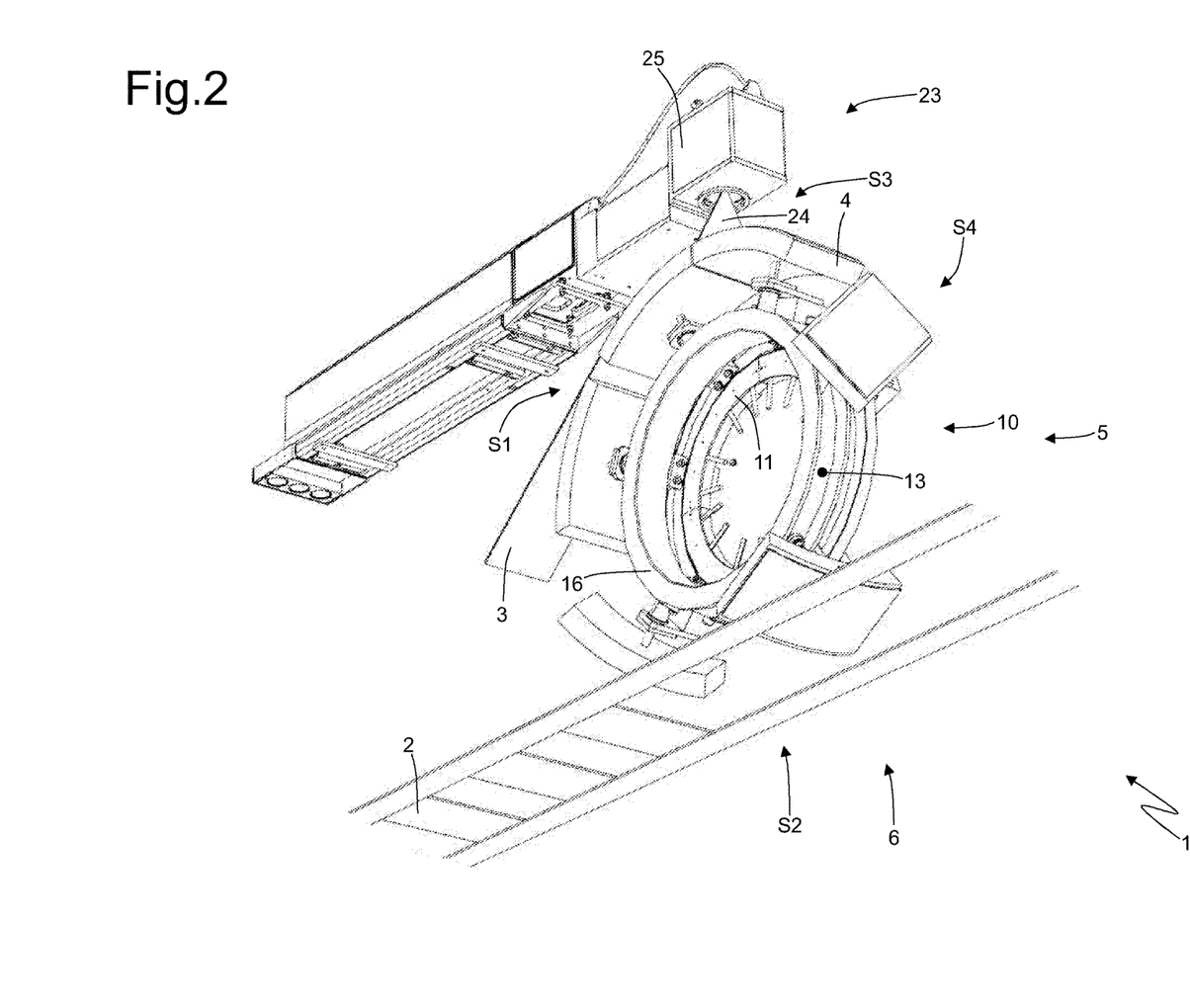
FIGS. 2 and 3 are two further perspective and schematic views of the feeding unit of FIG. 1.
Figure 3:
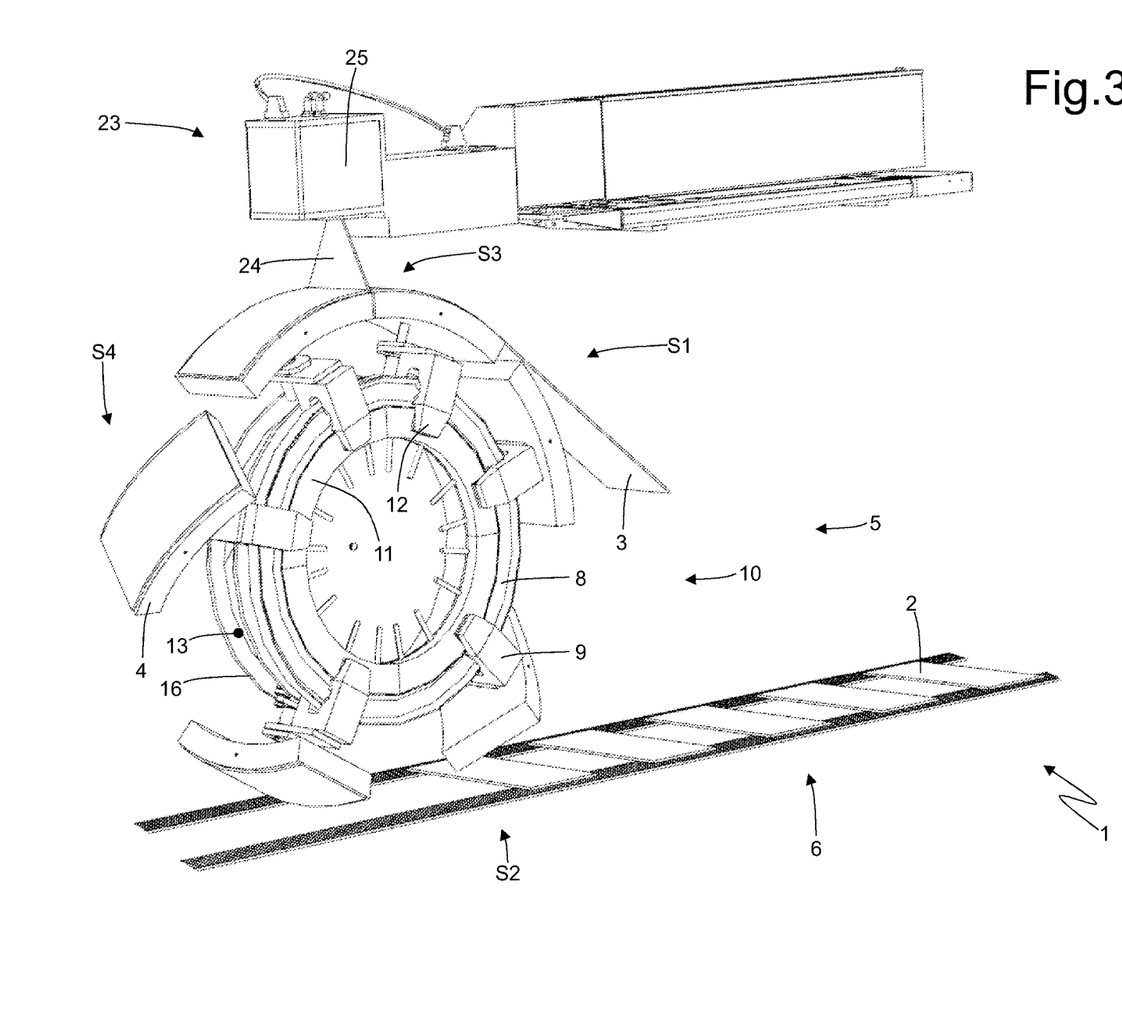

According to a preferred embodiment illustrated in FIGS. 1, 2 and 3, the conveyor 5 comprises a support element 16, which is arranged next to the guide 8 and in which the cam 13 is obtained. In other words, the cam 13 is obtained in the support element 16 which is at least initially separate and independent from the guide 8 and is arranged next to the guide 8.

According to what is illustrated in FIGS. 5, 6 and 7, each slide 9 is "U"-shaped and embraces the guide 8 on both sides of the guide 8 itself (as illustrated in FIG. 7); in other words, each slide 9 has two legs that are facing and opposing each other and embrace the guide 8 (i.e. between the two legs of the slide 9 a chamber is delimited which houses the guide 8). Each slide 9 supports a plurality of wheels 17, which are idly mounted on the slide 9 and roll along respective rolling surfaces 18 (illustrated in FIG. 7) of the guide 8; in particular, each leg of the slide 9 supports two pairs of wheels 17 (in each pair of wheels 17 the two wheels 17 are arranged side by side one with the other, while the two pairs of wheels 17 of the same leg of the slide 9 are opposite and oriented perpendicularly to one another). On each side the guide 8 comprises a pair of rolling surfaces 18 (illustrated in FIG. 7) which are arranged at a given distance from one another, are oriented perpendicularly to one another, and are coupled to corresponding wheels 17 of the slide 9. The presence of the wheels 17 allows each slide 9 to slide along the guide 18 with a very low friction and at the same time ensures a crosswise containment of the slide 9; i.e. each slide 9 can only slide along the guide 18 without making any movement perpendicular to the guide 18 itself.

According to what illustrated in FIGS. 5, 6 and 7, each slide 9 is provided with a bracket 19, which projects from the slide 9 itself and supports the sucking-holding head 4; in particular, the end of the bracket 19 that protrudes from the slide 9 has a through hole inside which a bearing, which carries a shaft supporting the corresponding sucking-holding head 4, is housed.

Figure 4:
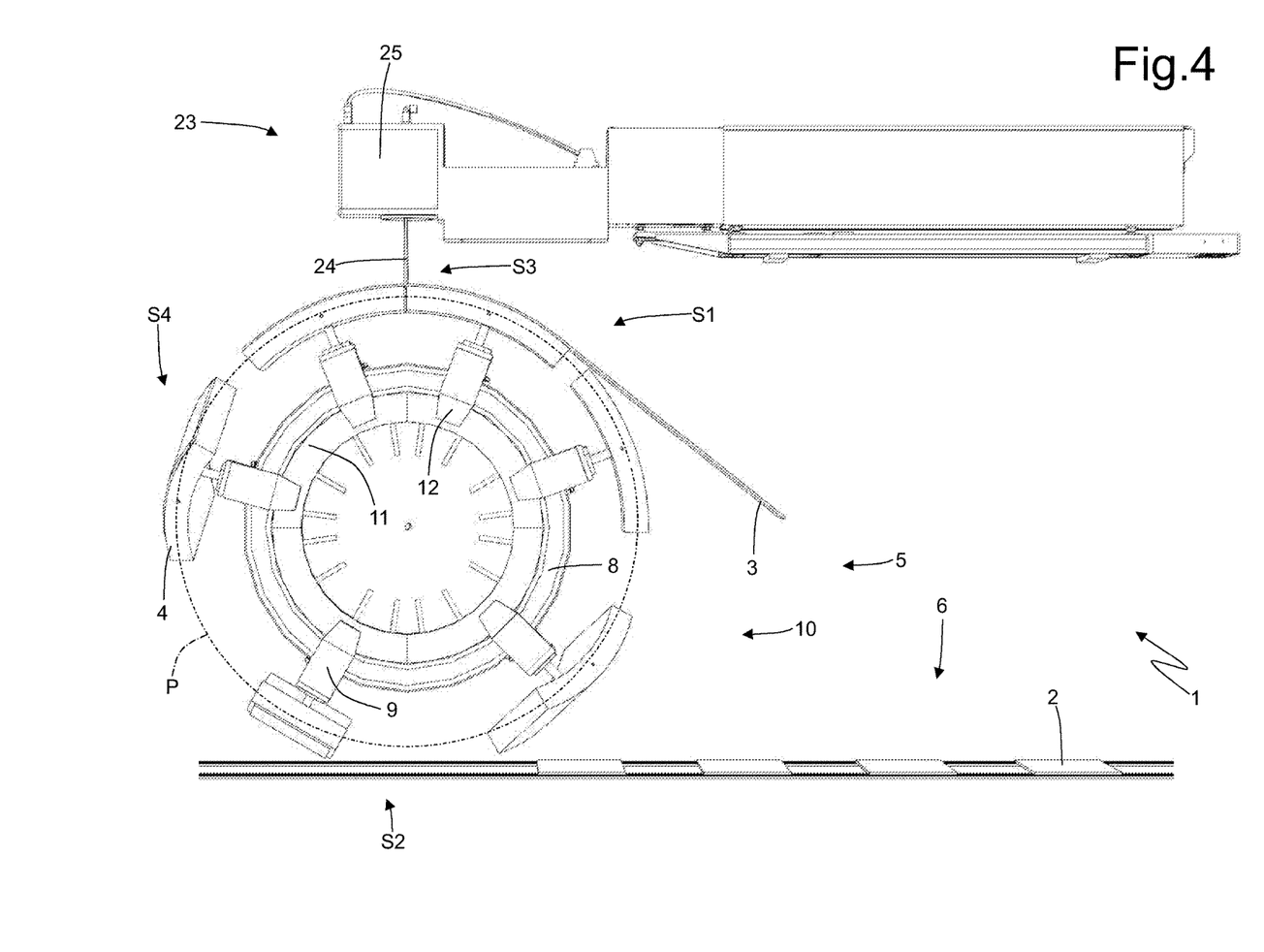
FIG. 4 is a schematic front view of the feeding unit of FIG. 1.

As illustrated more clearly in FIG. 4, the stator 11 of the linear electric motor 10 is arranged coplanar with the guide 8 and inside the guide 8 itself. In other words, the stator 11 of the linear electric motor 10 and the guide 8 are arranged on a same plane and one inside the other; in this way, the stator 11 of the linear electric motor 10 may be mechanically connected (typically by means of screws) to the guide 8. According to a preferred, but not binding, embodiment, the stator 11 of the linear electric motor 10 is divided into several sectors (four in FIG. 4, but could be more or less) which are arranged one after the other along the guide 8. The individual sectors of the stator 11 are mechanically and electrically independent one of the other, i.e. each sector of the stator 11 is electrically powered by its own driving device that is exclusively dedicated to its own sector (and therefore is different and separate from the driving devices of the other sectors); obviously has a central control unit which controls in a coordinated manner the four driving devices so as to move the slides 9 (and therefore the corresponding sucking-holding heads 4) along the application path P according to the desired law of motion.

Figure 8:
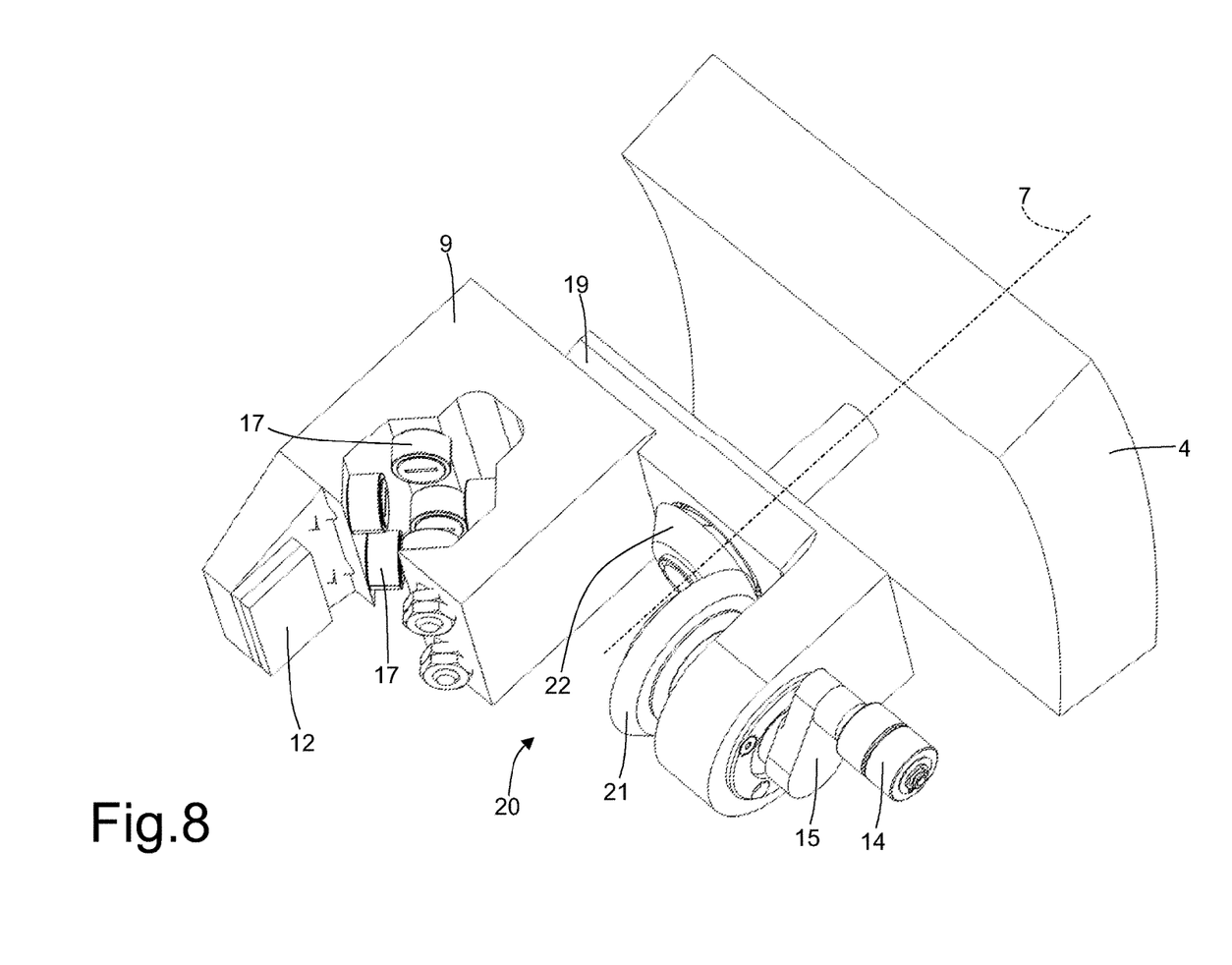
FIG. 8 is a front perspective view of an alternative of a mobile assembly of FIG. 5.

In the embodiment illustrated in FIGS. 1-7, the cam follower rollers 14 are oriented parallel to the corresponding rotation axes 7; in the alternative illustrated in FIG. 8, the cam follower rollers 14 are oriented perpendicularly to the corresponding rotation axes 7. As illustrated in FIG. 8, in each slide 9 operating arm 15 has a first end on which the cam follower rollers 14 is fitted in a rotary manner and a second end which is mechanically connected to the sucking-holding head 4 by means of a mechanical transmission 20. In the preferred, but not limiting, embodiment illustrated in FIG. 8, the mechanical transmission 20 comprises a toothed wheel 21 angularly integral with the operating arm 15 and a toothed wheel 22 which is angularly integral with the sucking-holding head 4 (in particular is keyed to a shaft which supports the sucking-holding head 4), meshes with the toothed wheel 21, and is perpendicularly oriented relative to the toothed wheel 21 itself.

According to a possible embodiment, each slide 9 receives the suction from the guide 8: on an outer surface of the guide 8 a chamber is obtained which internally communicates with a suction source and is externally open towards the slide 9; then each slide 9 transmits the suction to the corresponding sucking-holding head 4 by means of internal ducts provided with a pneumatic rotary joint at the shaft which supports the sucking-holding head 4 or by means of a flexible outer tube which is able to follow the 90° rotation of the sucking-holding head 4 around the rotation axis 7.

In use, the linear electric motor 10 is able to control the movement of each slide 9 (and therefore of each sucking-holding head 4) along the guide 8 (i.e. along the application path P) in a completely autonomous and independent manner from the others slides 9 (therefore from the other sucking-holding heads 4); accordingly, each slide 9 (therefore each sucking-holding head 4) is coupled to the guide 8 so as to freely slide along the guide 8 itself with a completely independent law of motion from the other slides 9 (therefore from the other sucking-holding heads 4). The law of motion of each slide 9 (therefore of each sucking-holding head 4) is dependent solely on the software control mode of the stator 11 of the linear electric motor 10; therefore, a modification of the laws of motion of the slides 9 (therefore of the sucking-holding heads 4) takes place only by acting on the software control of the stator 11 of the linear electric motor 10.

In the embodiments illustrated in the attached figures, the stator 11 of the linear electric motor 10 is arranged within the guide 8, i.e. the stator 11 of the linear electric motor 10 is arranged in contact with an inner surface of the guide 8. According to a different embodiment not illustrated, the stator 11 of the linear electric motor 10 is arranged outside the guide 8, i.e. the stator 11 of the linear electric motor 10 is arranged in contact with an outer surface of the guide 8. According to a further embodiment not illustrated, the stator 11 of the linear electric motor 10 is arranged beside the guide 8, i.e. the stator 11 of the linear electric motor 10 is arranged in contact with a side surface of the guide 8. Furthermore, in the embodiments illustrated in the attached figures, the stator 11 of the linear electric motor 10 is arranged coplanar with the guide 8, i.e. the lying plane of the stator 8 is parallel and coincident with the lying plane of the guide 8. According to a different embodiment not illustrated, the lying plane of the stator 8 is perpendicular to the lying plane of the guide 8. According to a further embodiment not illustrated, the lying plane of the stator 8 is parallel to the lying plane of the guide 8 but not coincident with the lying plane of the guide 8 itself. In the embodiments illustrated in the attached figures, the stator 11 of the linear electric motor 10 is arranged within the guide 8 (in contact with an inner surface of the guide 8) and the stator 11 of the linear electric motor 10 is arranged coplanar with the guide 8 (i.e. the lying plane of the stator 11 is parallel and coincident with the lying plane of the guide 8). According to a different embodiment not illustrated, the stator 11 of the linear electric motor 10 is arranged outside the guide 8 (in contact with an outer surface of the guide 8) and the lying plane of the stator 8 is perpendicular to the lying plane of the guide 8. According to a further embodiment not illustrated, the stator 11 of the linear electric motor 10 is arranged beside the guide 8 (in contact with a lateral surface of the guide 8) and the lying plane of the stator 8 is parallel to the lying plane of the guide 8 but not coincident with the lying plane of the guide 8 itself.

As illustrated in FIGS. 1-4, in the cutting station S3 a cutting device 23 is arranged which cyclically cuts the continuous web 3 crosswise, so as to separate the component 2 held by a sucking-holding head 4 from the remaining part of the continuous web 3. In the embodiment illustrated in FIGS. 1-4, the cutting device 23 is of laser type, i.e. operates by means of a laser beam 24 which cuts the continuous web 3 crosswise; in other words, the cutting device 23 comprises an emitter 25 which emits the laser beam 24 which cuts into the continuous web 3 and moves the continuous web 3 crosswise from one edge to the other of the continuous web 3 (i.e. along the whole crosswise extension of the continuous web 3) to sublimate the continuous web 3 along a cutting line. When the continuous web 3 is "hit" by the laser beam 24, the material that forms the continuous web 3 evaporates, i.e. sublimates, rapidly assuming a gaseous state at the point where it is cut, namely becomes smoke (normally at least partially visible).

The laser beam 24 is capable to cut the continuous web 3 crosswise quickly and accurately with no need for any type of contrast arranged on the opposite side of the continuous web 3 relative the laser beam 24 itself; consequently, between the sucking-holding heads 4 no kind of cutting contrast is provided and therefore the sucking-holding heads 4 are entirely free to rotate around the corresponding rotation axes 7 without any kind of mechanical impediment.

According to a possible (but not limiting) embodiment, the conveyor 5 advances with continuous motion (i.e. at a substantially constant speed and without stopping steps) the holding head 4 along the application path P, and the emitter 25 moves the laser beam 24 along an oblique direction relative to the application path P. The inclination (generally of a few degrees) of the cutting line followed by the laser beam 24 relative the application path P compensates for the displacement (minimal) of the continuous web 3 along the application path P during the performing of the crosswise cut so that the crosswise cut is perfectly perpendicular to the continuous web 3. The inclination of the cutting line followed by the laser beam 24 relative to the application path P is greater as is greater the feeding speed of the sucking-holding heads 4 along the application path P, namely the inclination of the cutting line followed by the laser beam 24 relative to the application path P it is not constant but varies as a function of the feeding speed of the sucking-holding heads 4 along the application path P.

According to a different embodiment not illustrated, the conveyor 5 illustrated in FIGS. 1-4 is replaced by a conventional drum that is fitted in a rotary manner around a central rotation axis and supports the sucking-holding heads 4; obviously in this case the application path P necessarily has a circular shape.

In the embodiment illustrated in FIGS. 1-4, the application path P is circular. Whereas, in the alternative embodiments illustrated in FIGS. 9-12, the application path P has an oval shape (i.e. a substantially elliptical shape) having two rectilinear segments parallel and opposite to each other which are connected by two curved segments opposite one to the other (preferably, but not necessarily, the two curvilinear segments are semicircular). Namely, the feeding path P has an oval shape comprising two opposite curved segments, preferably semicircular, and two straight segments which are opposite one to the other and join the two curved segments to one another.

In the embodiments illustrated in FIGS. 9-12, the cutting station S3 and the rotation station S4 are arranged one after the other along the same straight segment of the feeding path P; furthermore, in the embodiments illustrated in FIGS. 9-12 the input station S1 and the output station S2 are arranged along two different rectilinear segments of the feeding path P opposite one to the other.

The oval shaped application path P allows to move the cutting station S3 apart from the rotation station S4 as the rectilinear segments of the feeding path P are relatively long. Similarly, the oval shaped application path P allows to lengthen the output station S2 as each sucking-holding head 4 can remain parallel to and facing the device 6 for a particularly long segment of the application path P; in this way, the transfer of the components 2 to the device 6 can take place in a more accurate and precise manner even when operating at high hourly productivity.

Figure 9:
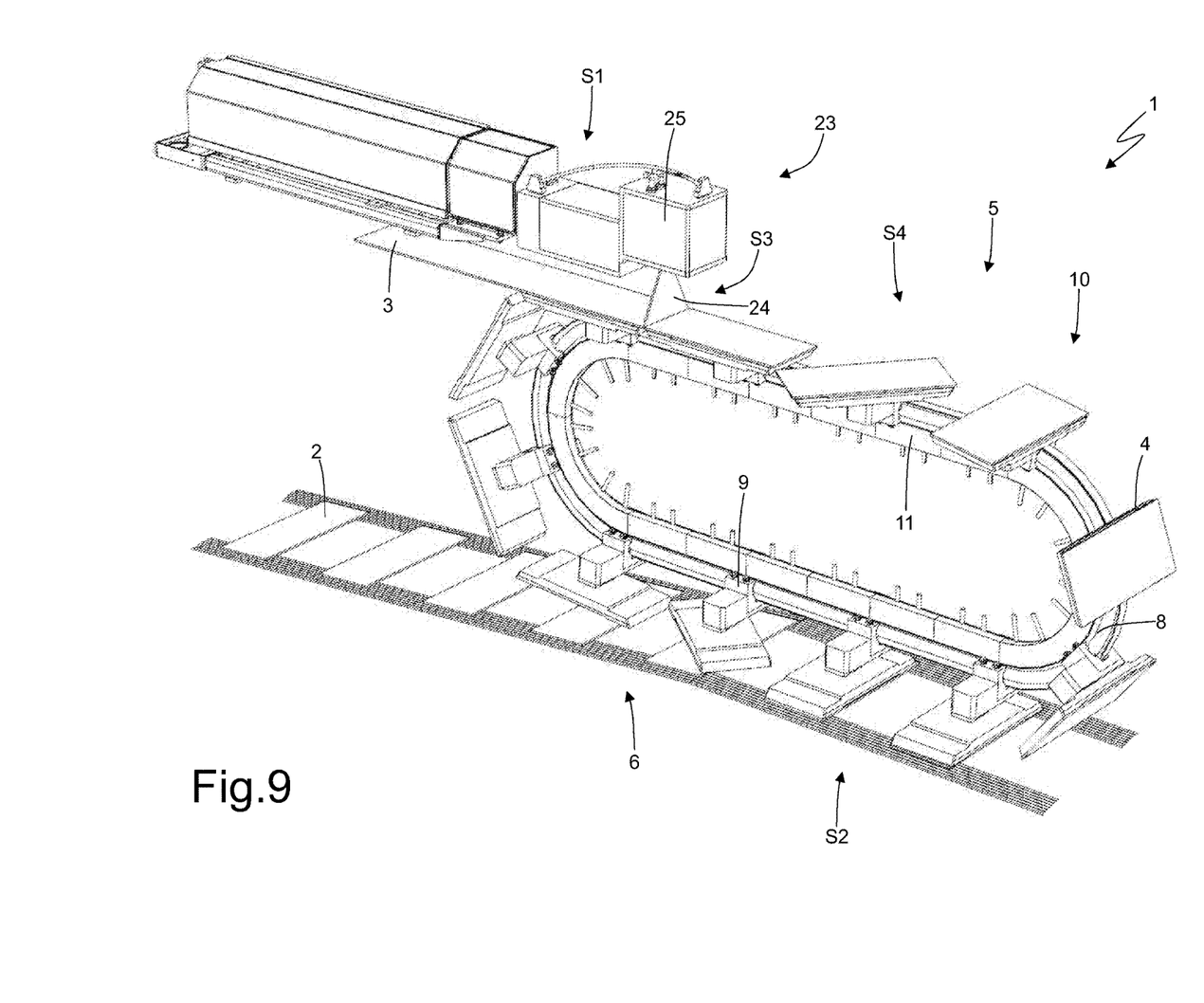
FIG. 9 is a perspective and schematic view of a different embodiment of a feeding unit of a component of a hygiene absorbent article made according to the present invention.
Figure 10:
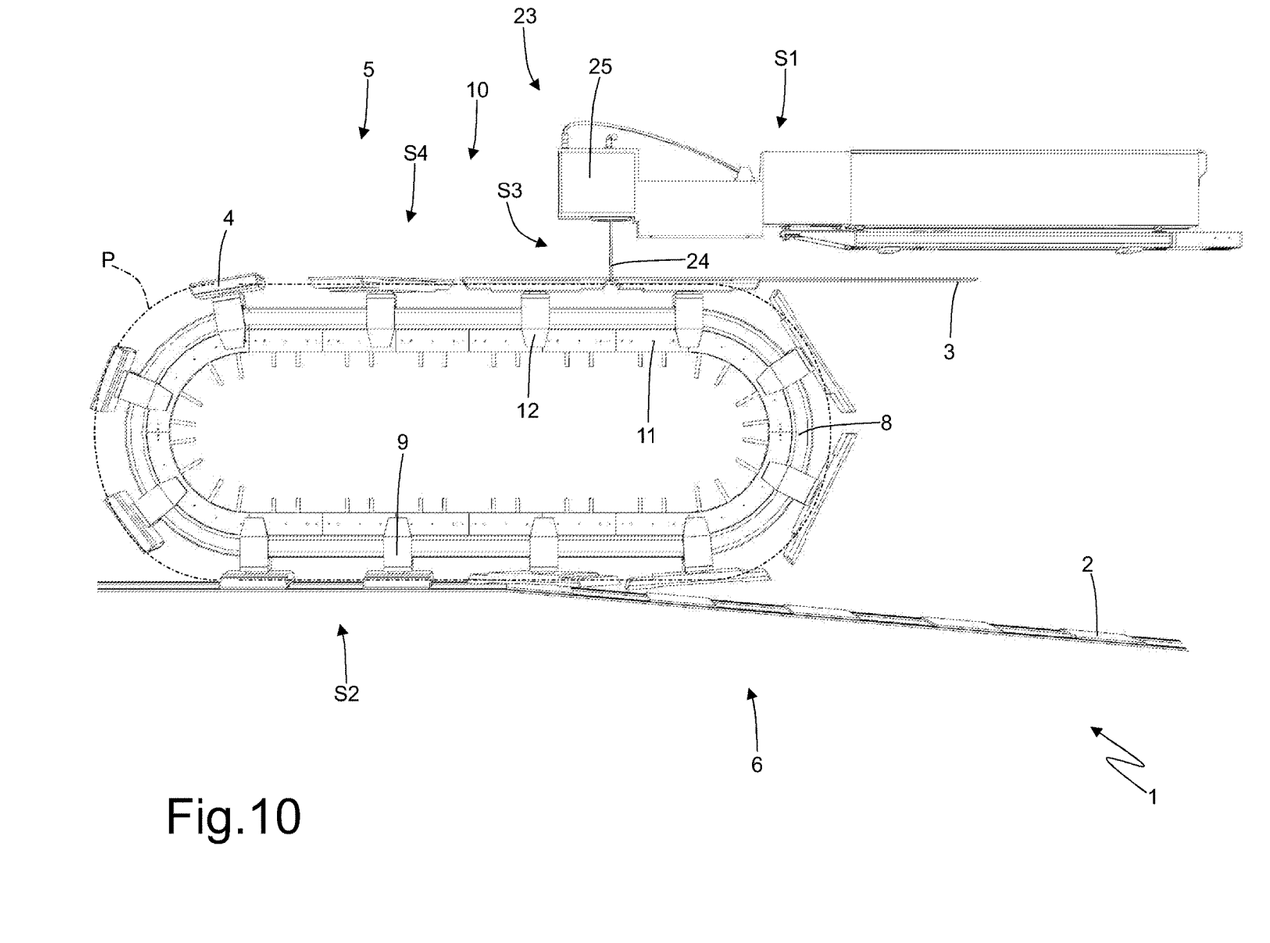
FIG. 10 is a schematic front view of the feeding unit of FIG. 9.
Figure 11:
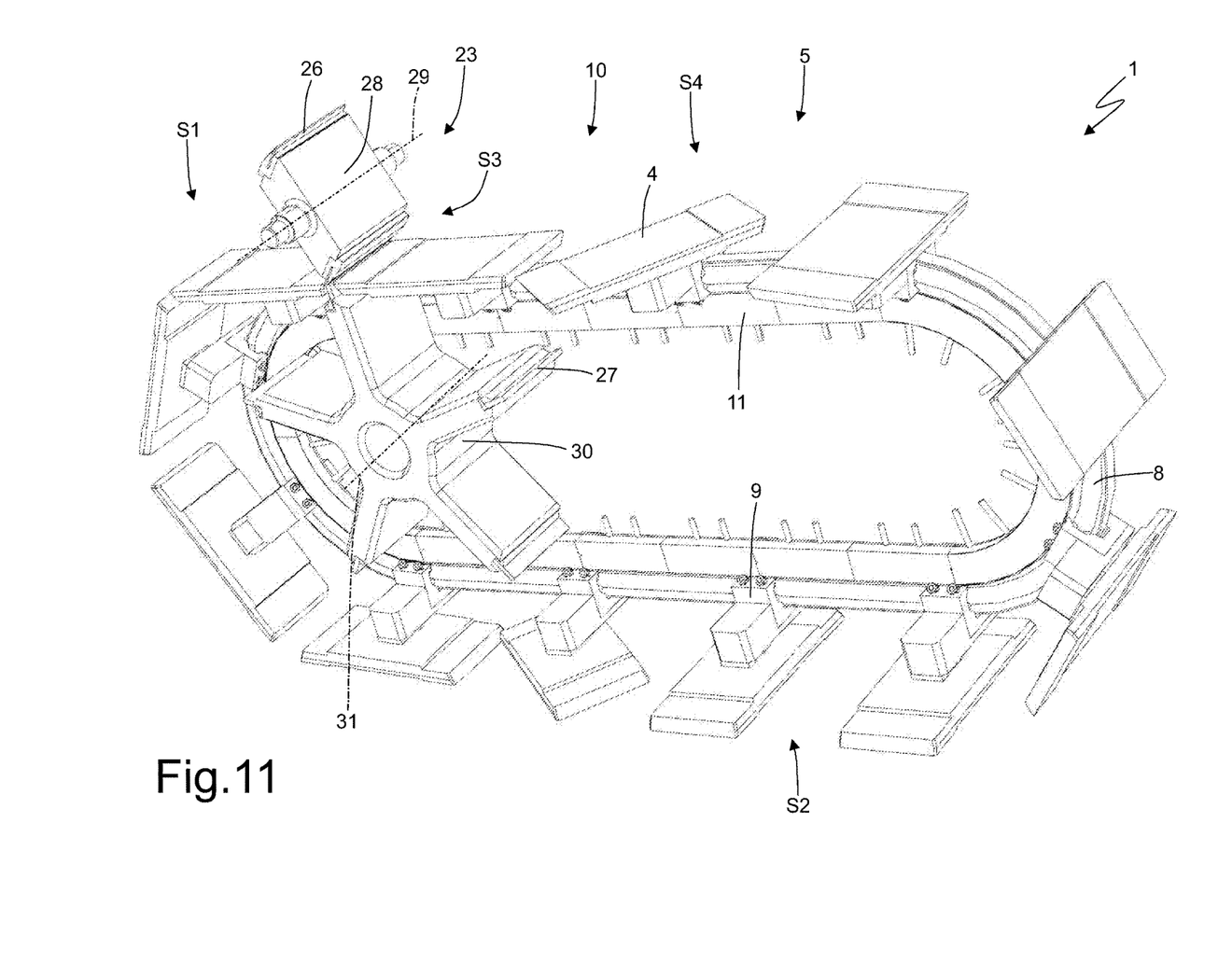
FIG. 11 is a schematic perspective view of a further embodiment of a unit for feeding a component of a hygiene absorbent article made according to the present invention.
Figure 12:
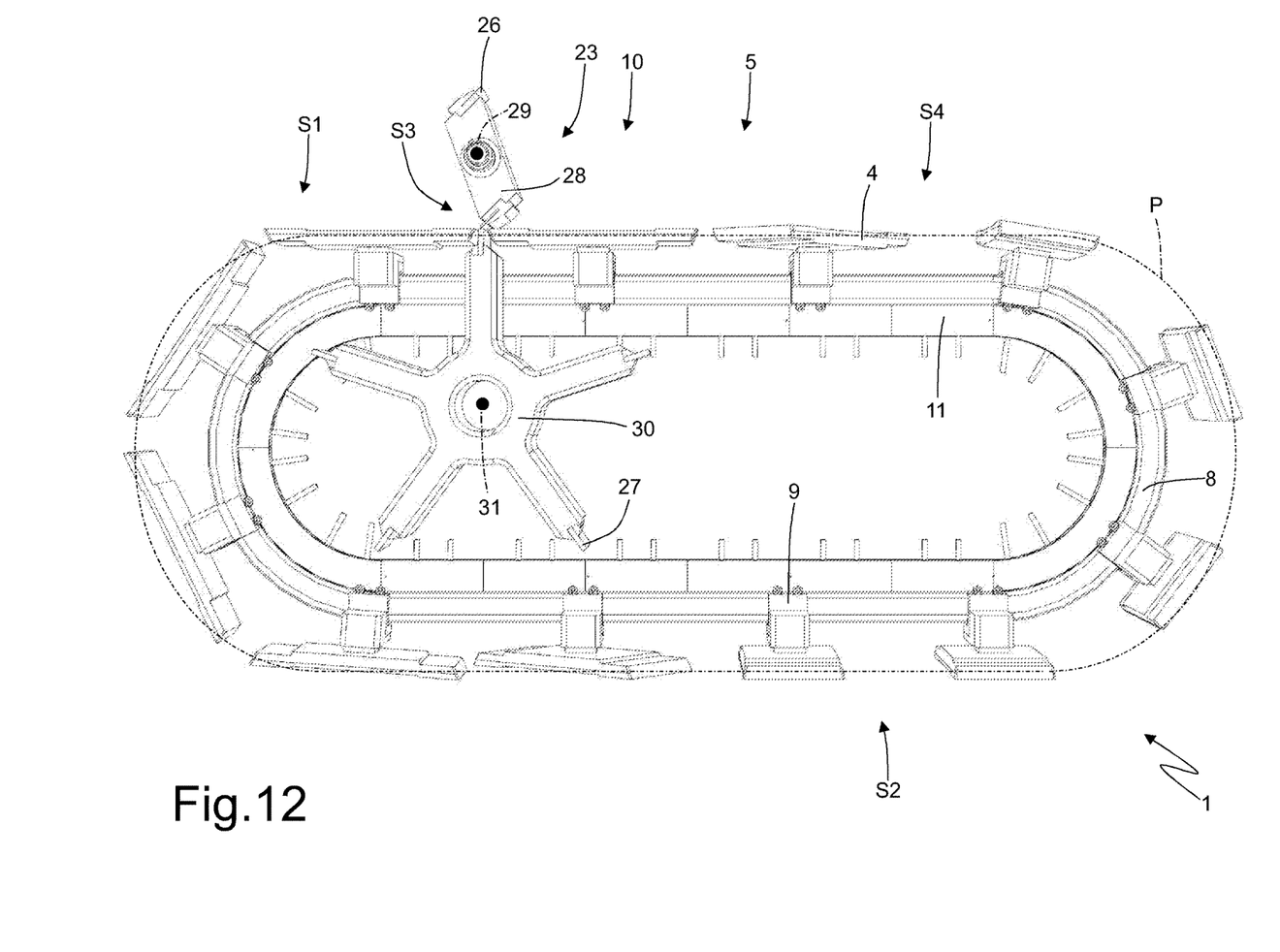
FIG. 12 is a schematic front view of the feeding unit of FIG. 11.

In the embodiment illustrated in FIGS. 9 and 10, the cutting device 23 is of laser type, i.e. of the type illustrated in FIGS. 1-4. In the alternative embodiment illustrated in FIGS. 11 and 12, the cutting device 23 is of a mechanical type and thus comprises a couple of blades 26 and a plurality of counter-blades 27 (i.e. anvils) cooperating with one another so as to cut the continuous web 3 crosswise. The two blades 26 (but obviously their number can be completely different) are carried by a cutting drum 28 which is arranged on one side of the application path P and rotates around a rotation axis 29 (perpendicular to the application path P) so as to cyclically allow each blade 26 to come into contact with the continuous web 3; similarly the counter-blades 27 are carried by a counter-drum 30, which is arranged on one side of the application path P opposite to the cutting drum 28 and rotates around a rotation axis 31 (parallel to the rotation axis 29) to cyclically allow each counter-blade 27 to come into contact with the continuous web 3 from the opposite side of the corresponding blade 26.

According to a preferred (but not binding) embodiment, the counter-drum 30 is arranged next to the guide 8; in this way, the counter-drum 30 does not interfere with the movement of the slides 9 (and therefore of the sucking-holding heads 4) along the feeding path P. According to a preferred, but not binding, embodiment illustrated in the attached figures, the cutting drum 28 is star shaped and has a series of radially oriented arms, each of which supports a corresponding counter-blade 27. According to the embodiment (not binding) illustrated in the accompanying figures, the cutting drum 28 supports two blades 26 opposite one to the other, whereas the counter-drum 30 supports five counter-blades 27, but obviously the number of blades 26 and/or counter-blades 27 can be completely different.

It is important to note that the components 2 which are fed by the feeding unit 1 can be any type of components used for manufacturing hygiene absorbent articles.

The feeding unit 1 described above has numerous advantages.

In the first place, in the feeding unit 1 described above is possible to obtain the rotation of each sucking-holding head 4 around the corresponding rotation axis 7 without any mechanical interference problem with parts of the cutting device 23. In the embodiment illustrated in FIGS. 1-4 and 9-10 this result is achieved by using a device 23 of laser cutting type that does not require a cutting contrast arranged between the sucking-holding heads 4. In the embodiment illustrated in FIGS. 11-12, this result is achieved by using an oval application path P which has a straight portion long enough to house, at a given distance from one another, the cutting station S3 and rotation station S4.

Furthermore, the feeding unit 1 described above does not use complex and expensive mechanical solutions as the two mobile units (the conveyor 5 and the counter-drum 30) separate and independent one from the other which must be integrated one with the other have a very wide space for use, which greatly simplifies the coexistence thereof.

Finally, in the feeding unit 1 described above a size change operation, i.e. an operation that modifies the maker machine to vary the type of hygiene absorbent articles which are manufactured, is extremely simple and fast, as the only physical change which may be required is the replacement of the sucking-holding heads 4, whereas the law of motion of the sucking-holding heads 4 (i.e. the slides 9) is modified thanks to an intervention on the control software. In other words, changing the law of motion of the sucking-holding heads 4 does not require the replacement of any mechanical component, but takes place entirely by way of software.

The invention claimed is:

1. A feeding unit (1) for feeding components (2) of a hygiene absorbent articles; the feeding unit (1) comprises:
    a plurality of sucking-holding heads (4), each of which is designed to receive and hold a corresponding component (2);
    a conveyor (5) to cyclically move each holding head (4) along an annular application path (P);
    an input station (S1), which is arranged along the application path (P) and in which each holding head (4) receives a corresponding component (2), which is connected—without gaps—to a continuous web (3);
    a cutting station (S3), which is arranged along the application path (P) downstream of the input station (S1) and is provided with a cutting device (23), which cuts the continuous web (3) crosswise, so as to separate the component (2) held by each holding head (4) from the remaining part of the continuous web (3); and
    an output station (S2), which is arranged along the application path (P) downstream of the rotation station (S4) and in which each holding head (4) releases the component (2);
    wherein the conveyor (5) comprises:
    an annular guide (8), which is arranged in a fixed position along the application path (P);
    a plurality of slides (9), each of which supports a corresponding holding head (4) and is coupled to the guide (8) so as to freely slide along the guide (8), and
    a linear electric motor (10), which comprises a single stator (11), which is arranged in a fixed position along the guide (8), and a plurality of mobile sliders (12), each of which is electro-magnetically coupled to the same stator (11) so as to receive, from the same stator (11), a driving force and is rigidly connected to a corresponding slide (9).

2. The feeding unit (1) according to claim 1, wherein the cutting device (23) comprises an emitter (25), which emits a laser beam (24), which cuts into the continuous web (3) and moves across the continuous web (3), from an edge to the other of the continuous web (3), so as to sublimate the continuous web (3) along a cutting line.

3. The feeding unit (1) according to claim 1, wherein the cutting device (23) comprises:
    at least one blade (26) and at least one counter-blade (27) cooperating with one another so as to cut the continuous web (3) crosswise;
    a cutting drum (28), which is arranged on one side of the application path (P), supports the blade (26), and rotates around a first rotation axis (29) so as cyclically allow the blade (26) to come into contact with the continuous web (3), and
    a counter-drum (30), which is arranged on one side of the application path (P) opposite the cutting drum (28), supports the counter-blade (27), and rotates around a second rotation axis (31) so as cyclically allow the counter-blade (27) to come into contact with the continuous web (3) on the opposite side of the blade (26).

4. The feeding unit (1) according to claim 3, wherein the counter-drum (30) is arranged beside the guide (8).

5. The feeding unit (1) according to claim 3, wherein the feeding path (P) is circular.

6. The feeding unit (1) according to claim 3, wherein the feeding path (P) has an oval shape comprising two opposite curved segments, preferably semicircular, and two opposite straight segments, which join the two curved segments to one another.

7. The feeding unit (1) according to claim 6, wherein the cutting station (S3) is arranged along a straight segment of the feeding path (P).

8. The feeding unit (1) according to claim 7 and comprising a rotation station (S4), which is arranged along the same straight segment of the feeding path (P) as the cutting station (S3), downstream of the cutting station (S3) and in which the holding head (4) rotates relative to the conveyor (5) so as to vary the orientation of the component (2).

9. The feeding unit (1) according to claim 6, wherein the input station (S1) and the output station (S2) are arranged along two different straight segments of the feeding path (P), which are opposite one another.

10. The feeding unit (1) according to claim 1, wherein:
    the sucking-holding head (4) is fitted on the slide (9) in a rotary manner, so as to rotate around a rotation axis (7); and
    an operating system is provided, in order to control the rotation of the sucking-holding head around the rotation axis (7).

11. The feeding unit (1) according to claim 10, wherein the operating system comprises:
    a cam (13), which is arranged in a fixed position beside the guide (8) and long the application path (P); and
    a cam follower roller (14), which is coupled to the cam (13) and is mechanically connected to the sucking-holding head (4).

12. The feeding unit (1) according to claim 11, wherein the conveyor (5) comprises a support element (16), which is arranged beside the guide (8) and in which the cam (13) is obtained.

13. The feeding unit (1) according to claim 1, wherein the slide (9) is "U"-shaped and embraces the guide (8) on both sides of the guide (8).

14. The feeding unit (1) according to claim 13, wherein the slide (9) supports a plurality of wheels (17), which are fitted on the slide (9) in an idle manner and roll along respective rolling surfaces of the guide (8).

15. The feeding unit (1) according to claim 14, wherein, on each side, the guide (8) comprises a pair of rolling surfaces (18), which are arranged at a given distance from one another, are oriented perpendicularly to one another, and are coupled to corresponding wheels (17) of the slide (9).

16. The feeding unit (1) according to claim 1, wherein a bracket (19) is provided, which projects from the slide (9) and supports the sucking-holding head (4).

17. The feeding unit (1) according to claim 1 and comprising a rotation station (S4), which is arranged along the feeding path (P) downstream of the cutting station (S3) and in which the holding head (4) rotates relative to the conveyor (5) so as to vary the orientation of the component (2).

* * * * *